United States Patent
Carroll et al.

(10) Patent No.: US 11,957,858 B2
(45) Date of Patent: Apr. 16, 2024

(54) WOUND THERAPY SYSTEM WITH INSTILLATION THERAPY AND DYNAMIC PRESSURE CONTROL

(71) Applicant: KCI LICENSING, INC., San Antonio, TX (US)

(72) Inventors: Christopher A. Carroll, San Antonio, TX (US); Brett L. Moore, San Antonio, TX (US); Shannon C. Ingram, Bulverde, TX (US); Justin Rice, San Antonio, TX (US)

(73) Assignee: 3M Innovative Properties Company, Saint Paul, MN (US)

( * ) Notice: Subject to any disclaimer, the term of this patent is extended or adjusted under 35 U.S.C. 154(b) by 868 days.

(21) Appl. No.: 16/567,025

(22) Filed: Sep. 11, 2019

(65) Prior Publication Data
US 2020/0078224 A1 Mar. 12, 2020

Related U.S. Application Data

(60) Provisional application No. 62/744,759, filed on Oct. 12, 2018, provisional application No. 62/730,214, filed on Sep. 12, 2018.

(51) Int. Cl.
| A61F 13/02 | (2006.01) |
| A61M 1/00 | (2006.01) |
| A61M 3/02 | (2006.01) |

(52) U.S. Cl.
CPC ....... *A61M 3/0258* (2013.01); *A61F 13/0216* (2013.01); *A61M 1/74* (2021.05);
(Continued)

(58) Field of Classification Search
CPC ....... A61F 13/0216; A61M 1/92; A61M 1/96; A61M 2205/3344
See application file for complete search history.

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 B2 | 3/1986 |
| AU | 745271 B2 | 3/2002 |

(Continued)

OTHER PUBLICATIONS

Louis C. Argenta, MD and Michael J. Morykwas, PhD; Vacuum-Assisted Closure: A New Method for Wound Control and Treatment: Clinical Experience; Annals of Plastic Surgery; vol. 38, No. 6, Jun. 1997; pp. 563-576.

(Continued)

*Primary Examiner* — Jessica Arble

(57) ABSTRACT

A wound therapy system includes a dressing an instillation pump fluidly communicable with the dressing and configured to provide instillation fluid to the dressing, a negative pressure pump fluidly communicable with the dressing and configured to remove air from the dressing, and a control circuit communicably coupled to the instillation pump and the negative pressure pump. The control circuit is configured to control the instillation pump to provide an amount of the instillation fluid to the dressing, provide a soak period, and control the negative pressure pump to provide a cyclic variation of negative pressure at the dressing.

33 Claims, 11 Drawing Sheets

(52) U.S. Cl.
CPC .............. *A61M 1/772* (2021.05); *A61M 1/92* (2021.05); *A61M 1/96* (2021.05); *A61M 3/0202* (2021.05); *A61M 1/915* (2021.05); *A61M 1/962* (2021.05); *A61M 2205/3344* (2013.01); *A61M 2205/3379* (2013.01)

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 7,846,141 B2 | 12/2010 | Weston | |
| 8,062,273 B2 | 11/2011 | Weston | |
| 8,216,198 B2 | 7/2012 | Heagle et al. | |
| 8,251,979 B2 | 8/2012 | Malhi | |
| 8,257,327 B2 | 9/2012 | Blott et al. | |
| 8,398,614 B2 | 3/2013 | Blott et al. | |
| 8,449,509 B2 | 5/2013 | Weston | |
| 8,529,548 B2 | 9/2013 | Blott et al. | |
| 8,535,296 B2 | 9/2013 | Blott et al. | |
| 8,551,060 B2 | 10/2013 | Schuessler et al. | |
| 8,568,386 B2 | 10/2013 | Malhi | |
| 8,679,081 B2 | 3/2014 | Heagle et al. | |
| 8,834,451 B2 | 9/2014 | Blott et al. | |
| 8,926,592 B2 | 1/2015 | Blott et al. | |
| 9,017,302 B2 | 4/2015 | Vitaris et al. | |
| 9,198,801 B2 | 12/2015 | Weston | |
| 9,211,365 B2 | 12/2015 | Weston | |
| 9,289,542 B2 | 3/2016 | Blott et al. | |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2009/0306609 A1 | 12/2009 | Blott et al. | |
| 2010/0298792 A1 | 11/2010 | Weston et al. | |
| 2011/0004172 A1* | 1/2011 | Eckstein | A61M 1/0023 604/313 |
| 2011/0196321 A1* | 8/2011 | Wudyka | A61M 1/784 604/319 |
| 2013/0211318 A1* | 8/2013 | Croizat | A61M 1/85 604/23 |
| 2014/0163491 A1 | 6/2014 | Schuessler et al. | |
| 2015/0080788 A1 | 3/2015 | Blott et al. | |
| 2015/0320434 A1 | 11/2015 | Ingram et al. | |
| 2016/0339158 A1* | 11/2016 | Collinson | A61M 1/985 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |

(56) References Cited

FOREIGN PATENT DOCUMENTS

| | | |
|---|---|---|
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |
| WO | WO-2014/178945 A1 | 11/2014 |
| WO | WO-2017/160412 A1 | 9/2017 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & dated Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians; Jul. 2007.

(56) References Cited

OTHER PUBLICATIONS

International Search Report and Written Opinion in International Application No. PCT/US2019/050512 dated Dec. 11, 2019.
Chinese Office Action for corresponding application 201980070547X, dated Oct. 26, 2023.

* cited by examiner

WOUND THERAPY SYSTEM WITH INSTILLATION THERAPY AND DYNAMIC PRESSURE CONTROL

CROSS-REFERENCE TO RELATED APPLICATIONS

This application claims the benefit of priority to U.S. Provisional Application No. 62/730,214, filed on Sep. 12, 2018, and U.S. Provisional Application No. 62/744,759, filed on Oct. 12, 2018, which are both incorporated herein by reference in their entireties.

BACKGROUND

The present invention relates generally to the field of treating wounds, and more particularly to negative pressure wound therapy systems with instillation therapy. Negative pressure wound therapy refers to the application of negative pressure (relative to atmospheric pressure) to a wound bed to facilitate healing of the wound bed. Negative pressure may be applied in coordination with instillation therapy, in which instillation fluid (e.g., cleansing fluid, medicated fluid, antibiotic fluid, irrigation fluid) is applied to the wound bed. Negative pressure therapy with instillation therapy may facilitate removal of wound exudate and other debris from the wound bed and otherwise support healing. The present disclosure provides improved systems and methods for treating wounds using negative pressure wound therapy and instillation therapy.

SUMMARY

One implementation of the present disclosure is a wound therapy system. The wound therapy system includes a dressing an instillation pump fluidly communicable with the dressing and configured to provide instillation fluid to the dressing, a negative pressure pump fluidly communicable with the dressing and configured to remove air from the dressing, and a control circuit communicably coupled to the instillation pump and the negative pressure pump. The control circuit is configured to control the instillation pump to provide an amount of the instillation fluid to the dressing, provide a soak period, and control the negative pressure pump to provide a cyclic variation of negative pressure at the dressing.

In some embodiments, the cyclic variation of negative pressure includes an oscillation of the pressure at the dressing across a pressure differential. In some embodiments, the pressure differential is approximately 100 mmHg. In some embodiments, the pressure differential is within a range between approximately 5 mmHg and 300 mmHg.

In some embodiments, the cyclic variation of negative pressure includes a first cycle and a second cycle. The pressure differential changes between the first cycle and the second cycle. In some embodiments, the pressure differential oscillates over time.

In some embodiments, the pressure differential is user-selectable. In some embodiments, a frequency of the cyclic variation of negative pressure is user-selectable.

In some embodiments, the dressing includes a perforated layer having a plurality of holes extending therethrough. In some embodiments, the dressing is coupleable to a wound bed. The cyclic variation of negative pressure deforms the wound bed at the holes. In some embodiments, the cyclic variation of negative pressure includes a plurality of cycles. Each cycle does an amount of work of within a range between approximately 2 mJ and 30 mJ for each of the plurality of holes.

In some embodiments, the control circuit is configured to simultaneously control the negative pressure pump to provide a cyclic variation of negative pressure at the dressing and control the instillation pump to provide the instillation fluid to the dressing.

In some embodiments, at least one of the amount of the instillation fluid or the soak period is user-selectable. In some embodiments, the control circuit is further configured to control the negative pressure pump to provide a substantially constant negative pressure at the dressing.

In some embodiments, the control circuit is further configured to repeatedly cycle through sequentially controlling the instillation pump to provide the amount of the instillation fluid to the dressing, providing the soak period, and controlling the negative pressure pump to provide the cyclic variation of negative pressure at the dressing. In some embodiments, the control circuit is further configured to repeatedly cycle through sequentially controlling the instillation pump to provide the amount of the instillation fluid to the dressing, providing the soak period, controlling the negative pressure pump to provide the cyclic variation of negative pressure at the dressing, and controlling the negative pressure pump to provide a substantially constant negative pressure to the wound bed.

Another implementation of the present disclosure is a method of treating a wound. The method includes providing an instillation pump in fluid communication with a dressing, providing a negative pressure pump in fluid communication with the dressing, supplying, by the instillation pump, an amount of instillation fluid to the dressing, waiting for a soak period, and operating the negative pressure pump to create a cyclic variation of negative pressure at the dressing.

In some embodiments, the cyclic variation of negative pressure includes an oscillation of the pressure at the dressing across a pressure differential. In some embodiments, the pressure differential is approximately 100 mmHg. In some embodiments, the pressure differential is in a range between approximately 5 mmHg and 300 mmHg.

In some embodiments, the cyclic variation of negative pressure includes a first cycle and a second cycle. The method includes changing the pressure differential between the first cycle and the second cycle. In some embodiments, the method includes oscillating the pressure differential over time. In some embodiments, the method includes receiving a user selection of the pressure differential. In some embodiments, the method includes receiving a user selection of a frequency of the cyclic variation of negative pressure.

In some embodiments, the method includes deforming, by the cyclic variation of negative pressure, a wound bed coupled to the dressing. In some embodiments, deforming the wound bed includes drawing the wound bed into a plurality of holes that extend through a layer of the dressing. In some embodiments, the method includes doing an amount of work on the wound bed within a range between approximately 2 mJ and 30 mJ for each of the plurality of holes for each of multiple cycles of the cyclic variation of negative pressure.

In some embodiments, the method includes simultaneously operating the negative pressure pump to create a cyclic variation of negative pressure at the dressing and controlling the instillation pump to provide the instillation fluid to the dressing.

In some embodiments, the method includes receiving a user selection of at least one of the amount of the instillation fluid or the soak period. In some embodiments, the method includes operating the negative pressure pump to create a substantially constant negative pressure at the dressing.

In some embodiments, the method includes repeatedly cycling through sequentially supplying, by the instillation pump, an amount of instillation fluid to the dressing, waiting for a soak period, and operating the negative pressure pump to create a cyclic variation of negative pressure at the dressing.

In some embodiments, the method includes repeatedly cycling through sequentially supplying, by the instillation pump, an amount of instillation fluid to the dressing, waiting for a soak period, operating the negative pressure pump to create a cyclic variation of negative pressure at the dressing, and operating the negative pressure pump to create a substantially constant negative pressure at the dressing.

Another implementation of the present disclosure is a wound therapy system. The wound therapy system includes an instillation pump fluidly communicable with the dressing and configured to provide instillation fluid to the dressing, a negative pressure pump fluidly communicable with the dressing and configured to remove air from the dressing, and a control circuit communicably coupled to the instillation pump and the negative pressure pump. The control circuit is configured to control the instillation pump to provide an amount of the instillation fluid to the dressing, provide a soak period, and control the negative pressure pump to provide a variation of negative pressure at the dressing, the variation characterized by a waveform.

In some embodiments, the waveform includes an amplitude having a maximum at a high pressure value and a minimum at a low pressure value and a frequency. In some embodiments, the amplitude is variable in a repeating pattern. In some embodiments, the frequency is variable in a repeating pattern. In some embodiments, the amplitude is variable in a first repeating pattern and the frequency is variable in a second repeating pattern. In some embodiments, the waveform is user-selectable.

In some embodiments, the control circuit is configured to simultaneously control the negative pressure pump to provide the variation of negative pressure at the dressing and control the instillation pump to provide the instillation fluid to the dressing.

DETAILED DESCRIPTION

Negative Pressure and Instillation Wound Therapy System

Figure 1:
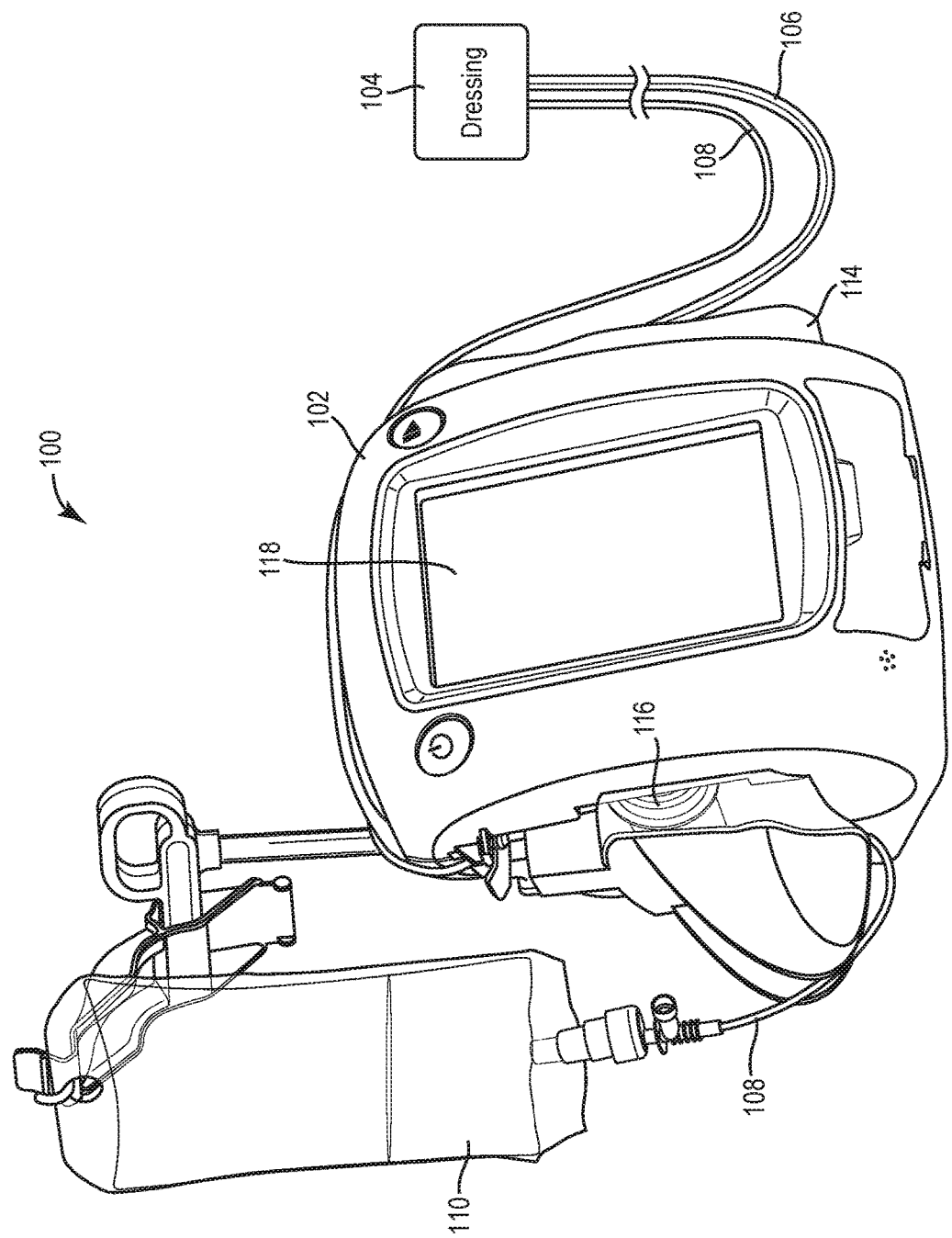
FIG. 1 is a perspective view of a negative pressure and instillation wound therapy system, according to an exemplary embodiment.
Figure 2:
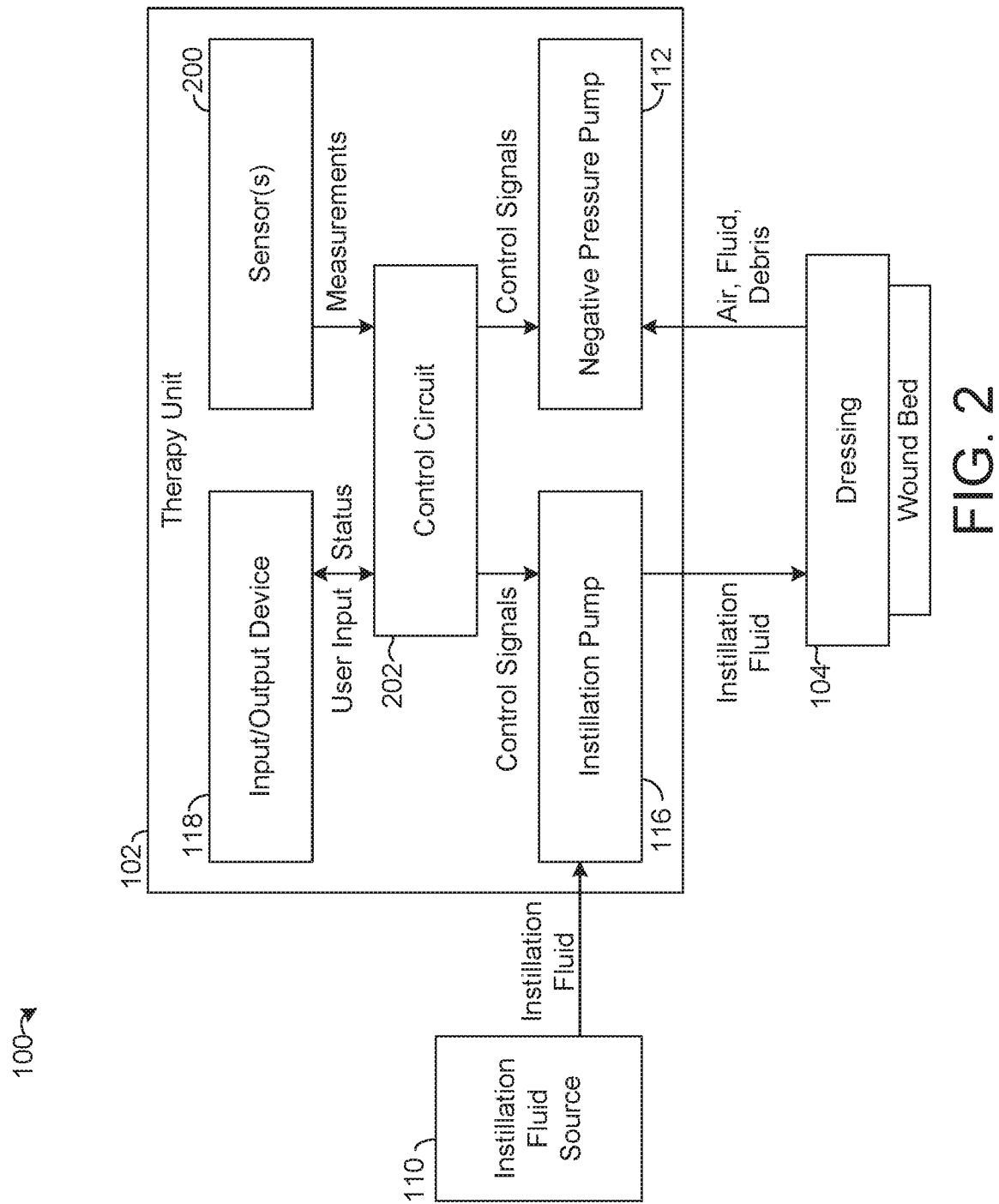
FIG. 2 is a block diagram of the negative pressure and instillation wound therapy system of FIG. 1, according to an exemplary embodiment.

Referring to FIGS. 1 and 2, a negative pressure and instillation wound therapy (NPIWT) system 100 is shown, according to exemplary embodiments. FIG. 1 shows a perspective view of the NPIWT system 100, according to an exemplary embodiment. FIG. 2 shows a block diagram of the NPIWT system 100, according to an exemplary embodiment. The NPIWT system 100 is shown to include a therapy unit 102 fluidly coupled to a dressing 104 via a vacuum tube 106 and an instillation tube 108. The NPIWT system 100 is also shown to include an instillation fluid source 110 fluidly coupled to the instillation tube 108. The NPIWT system 100 is configured to provide negative pressure wound therapy at a wound bed by reducing the pressure at the dressing 104 relative to atmospheric pressure. The NPIWT system 100 is also configured to provide instillation therapy by providing instillation fluid to the dressing 104. Furthermore, as described in detail herein, the NPIWT system 100 is configured to provide debridement of the wound bed and removal of undesirable fluid and debris from the wound bed.

Figure 6:
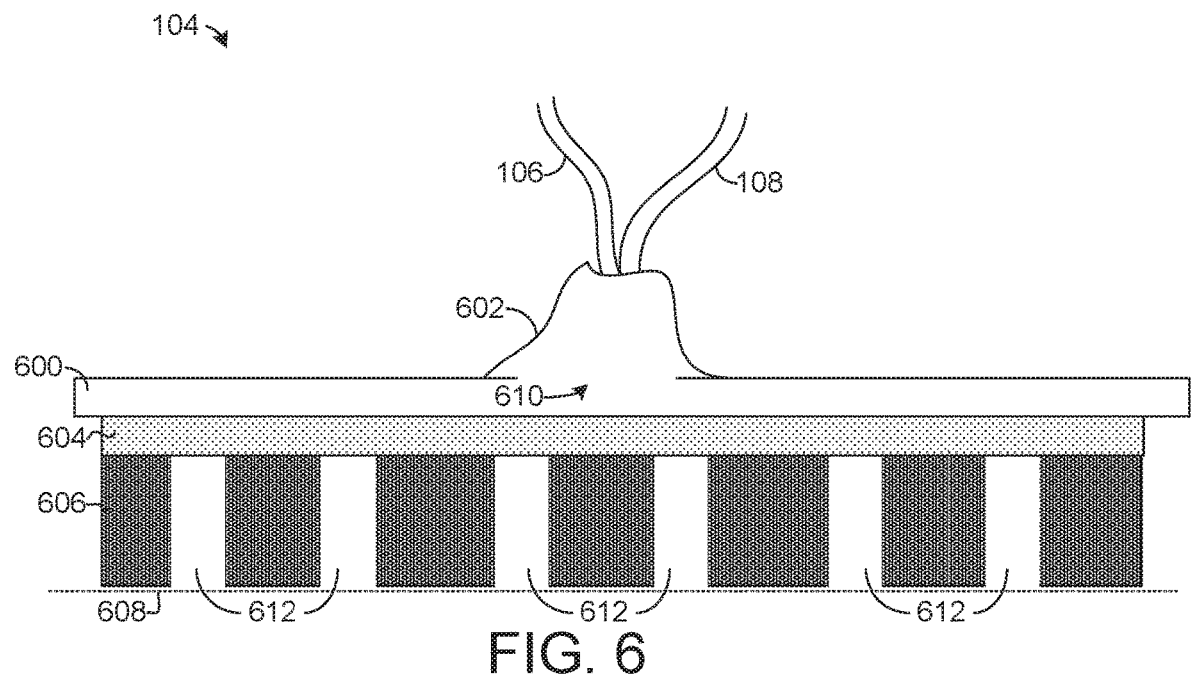
FIG. 6 is a cross-sectional side view of a dressing for use with the negative pressure and instillation wound therapy system of FIG. 1, according to an exemplary embodiment.
Figure 7:
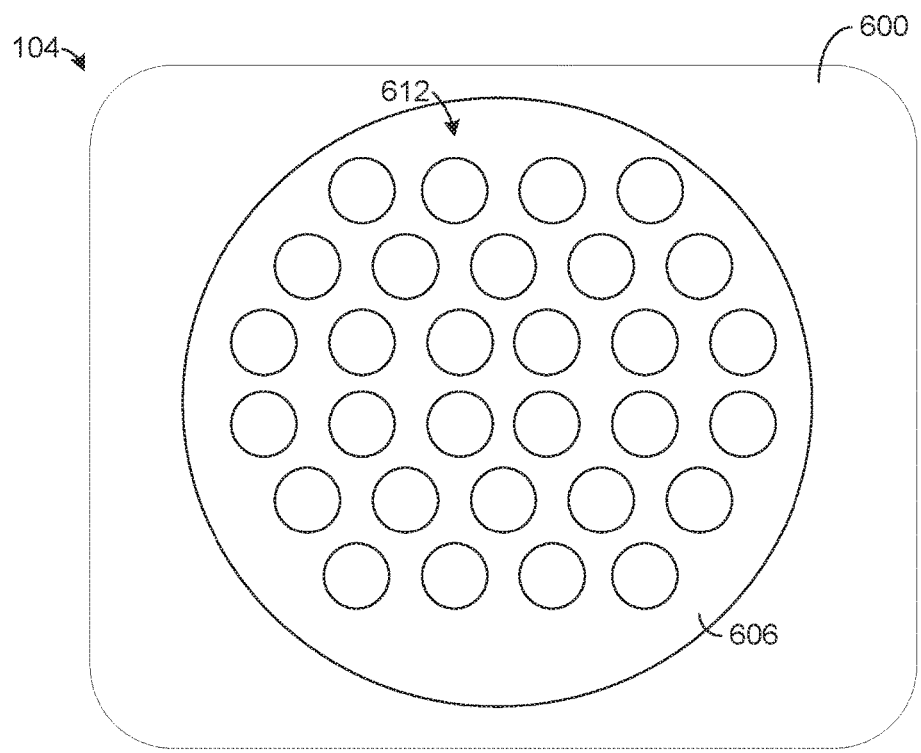
FIG. 7 is a bottom view of a dressing for use with the negative pressure and instillation wound therapy system of FIG. 1, according to an exemplary embodiment.

The dressing 104 is coupleable to a wound bed, i.e., a location of a wound (e.g., sore, laceration, burn, etc.) on a patient. The dressing 104 may be substantially sealed over the wound bed such that a pressure differential may be maintained between the atmosphere and the wound bed (i.e., across the dressing 104). The dressing 104 may be coupled to the vacuum tube 106 and the instillation tube 108, for example to place the vacuum tube 106 and/or the instillation tube 108 in fluid communication with the wound bed. An example embodiment of dressing 104 is shown in FIGS. 6-7 and described in detail with reference thereto. In some embodiments, the dressing 104 may be a V.A.C. VERAFLO™ dressing by Acelity or a V.A.C. VERAFLO CLEANSE CHOICE™ dressing by Acelity.

The therapy unit 102 includes a negative pressure pump 112 (shown in FIG. 2 and obscured within the therapy unit 102 in the perspective view of FIG. 1) configured to pump air, wound exudate, and/or other debris (e.g., necrotic tissue) and/or fluids (e.g., instillation fluid) out of the dressing 104 via the vacuum tube 106, thereby creating a negative pressure at the dressing 104. The negative pressure pump 112 is fluidly communicable with the vacuum tube 106 and the dressing 104. Wound exudate and/or other debris and/or fluids removed from the wound bed by the negative pressure pump 112 may be collected in a canister 114 located on the therapy unit 102.

Operating the negative pressure pump 112 may therefore both create a negative pressure at the wound bed and remove undesirable fluid and debris from the wound bed. In some cases, operating the negative pressure pump 112 may cause deformation of the wound bed and/or provide other energy to the wound bed to facilitate debridement and healing of the wound bed. As described in detail below, the negative pressure pump 112 may be operated in accordance with one or more dynamic pressure control approaches that may facilitate wound healing.

The therapy unit 102 also includes an instillation pump 116. The instillation pump 116 is configured to selectively provide instillation fluid from the instillation fluid source 110 to the dressing 104. The instillation pump 116 is operable to control the timing and amount (volume) of instillation fluid provided to the dressing 104. As described in detail below, the instillation pump 116 may be controlled in coordination with the negative pressure pump 112 to provide one or more wound treatment cycles that may facilitate wound healing.

The therapy unit 102 also includes an input/output device 118. The input/output device 118 is configured to provide information relating to the operation of the NPIWT system 100 to a user and to receive user input from the user. The input/output device 118 may allow a user to input various preferences, settings, commands, etc. that may be used in controlling the negative pressure pump 112 and the instillation pump 116 as described in detail below. The input/output device 118 may include a display (e.g., a touchscreen), one or more buttons, one or more speakers, and/or various other devices configured to provide information to a user and/or receive input from a user.

As shown in FIG. 2, the therapy unit 102 is also shown to include one or more sensors 200 and a control circuit 202. The sensor(s) 200 may be configured to monitor one or more of various physical parameters relating to the operation of the NPIWT system 100. For example, the sensor(s) 200 may measure pressure at the vacuum tube 106, which may be substantially equivalent and/or otherwise indicative of the pressure at the dressing 104. As another example, the sensor(s) 200 may measure an amount (e.g., volume) of instillation fluid provided to the dressing 104 by the instillation pump 116. The sensor(s) 200 may provide such measurements to the control circuit 202.

The control circuit 202 is configured to control the operation of the therapy unit 102, including by controlling the negative pressure pump 112, the instillation pump 116, and the input/output device 118. The control circuit 202 may receive measurements from the sensor(s) 200 and/or user input from the input/output device 118 and use the measurements and/or the user input to generate control signals for the instillation pump 116 and/or the negative pressure pump 112. As described in detail with reference to FIGS. 3-12 below, the control circuit 202 may control the negative pressure pump 112 and the instillation pump 116 to provide various combinations of various instillation phases, soak periods, and negative pressure phases to support and encourage wound healing.

Figure 3:
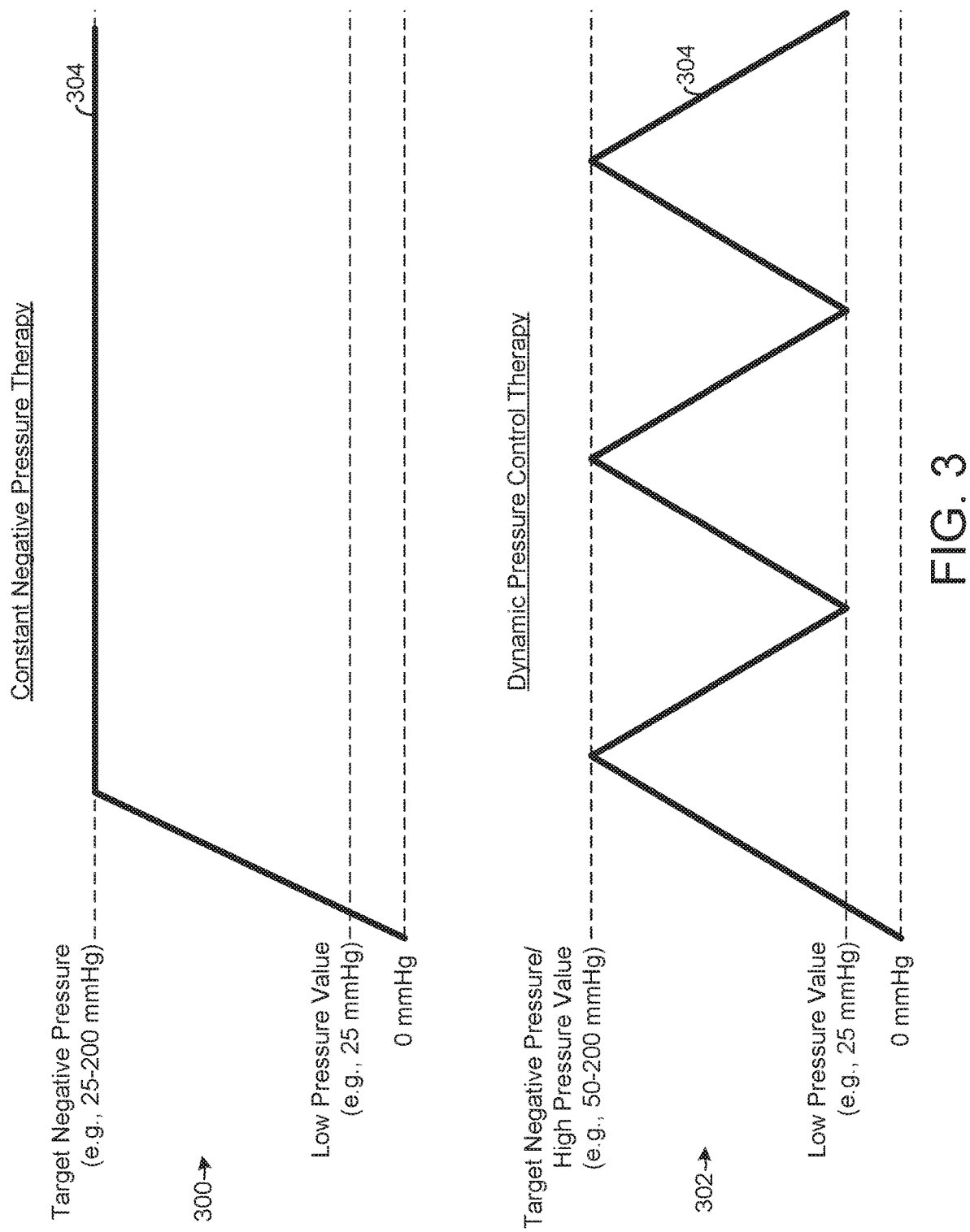
FIG. 3 is an illustration of negative pressure waveforms, according to an exemplary embodiment.

Referring now to FIG. 3, graphical representations of constant negative pressure therapy and dynamic pressure control therapy are shown, according to exemplary embodiments. A first graph 300 illustrates constant negative pressure therapy while a second graph 302 illustrates dynamic pressure control therapy. The graphs 300-302 show pressure at the dressing 104 on the vertical axis and time on the horizontal axis. The graphs 300-302 both include a pressure line 304 that illustrates the pressure at the dressing 104 over time. The control circuit 202 is configured to control the negative pressure pump 112 to achieve the pressure trajectories illustrated by the pressure lines 304.

As illustrated by graph 300, the control circuit 202 may control the negative pressure pump 112 to remove air, fluid, debris, etc. from the dressing 104 to reduce the pressure at the dressing 104 from atmospheric pressure to a target negative pressure. The control circuit 202 may then control the negative pressure pump 112 to maintain the pressure at the dressing 104 at approximately the target negative pressure. In some embodiments, the control circuit 202 may use pressure measurements from the sensor(s) 200 as feedback to facilitate maintenance of the pressure at approximately the target negative pressure. In the embodiment shown, the target negative pressure may be any value from approximately 25 mmHg to 200 mmHg. For example, in some embodiments, the target negative pressure may be user-selectable via the input/output device 118.

As illustrated by graph 302, the control circuit 202 may control the negative pressure pump 112 to provide a cyclic variation of negative pressure at the dressing 104. The control circuit 202 may control the negative pressure pump 112 to remove air, fluid, debris, etc. from the dressing 104 to reduce the pressure at the dressing 104 from atmospheric pressure to a target negative pressure (e.g., a high pressure value). The control circuit 202 may then control the negative pressure pump 112 to facilitate the pressure at the dressing 104 in returning to a low pressure value. That is, the negative pressure pump 112 may allow the pressure to drift back towards atmospheric pressure, for example by putting the dressing in fluid communication with the atmosphere, allowing air to leak into the dressing 104, and/or the negative pressure pump 112 pumping air into the dressing 104. When the pressure at the dressing 104 reaches a low pressure value (e.g., as detected by the sensor(s) 200) the control circuit 202 may control the negative pressure pump 112 to remove air, fluid, debris, etc. from the dressing 104 to reduce the pressure at the dressing 104 from the low pressure value to the target negative pressure (e.g., the high pressure value).

As illustrated by graph 302, the control circuit 202 may cause the cycle between a low pressure value and a high pressure value to be repeated multiple times. The low pressure value and the high pressure value may be user selectable. For example, the low pressure value may be approximately 25 mmHg and the high pressure value may be in the range of approximately 50 mmHg to approximately 200 mmHg. In some embodiments, the low pressure value may be 0 mmHg (i.e., atmospheric pressure). In other words, the control circuit 202 may control the negative pressure pump 112 to oscillate the pressure at the dressing 104 across a pressure differential. The pressure differential may be any value within a range between approximately 5 mmHg and approximately 300 mmHg, for example 100 mmHg (i.e., an oscillation between 25 mmHg and 125 mmHg is an oscillation across a pressure differential of 100 mmHg).

Figure 10:
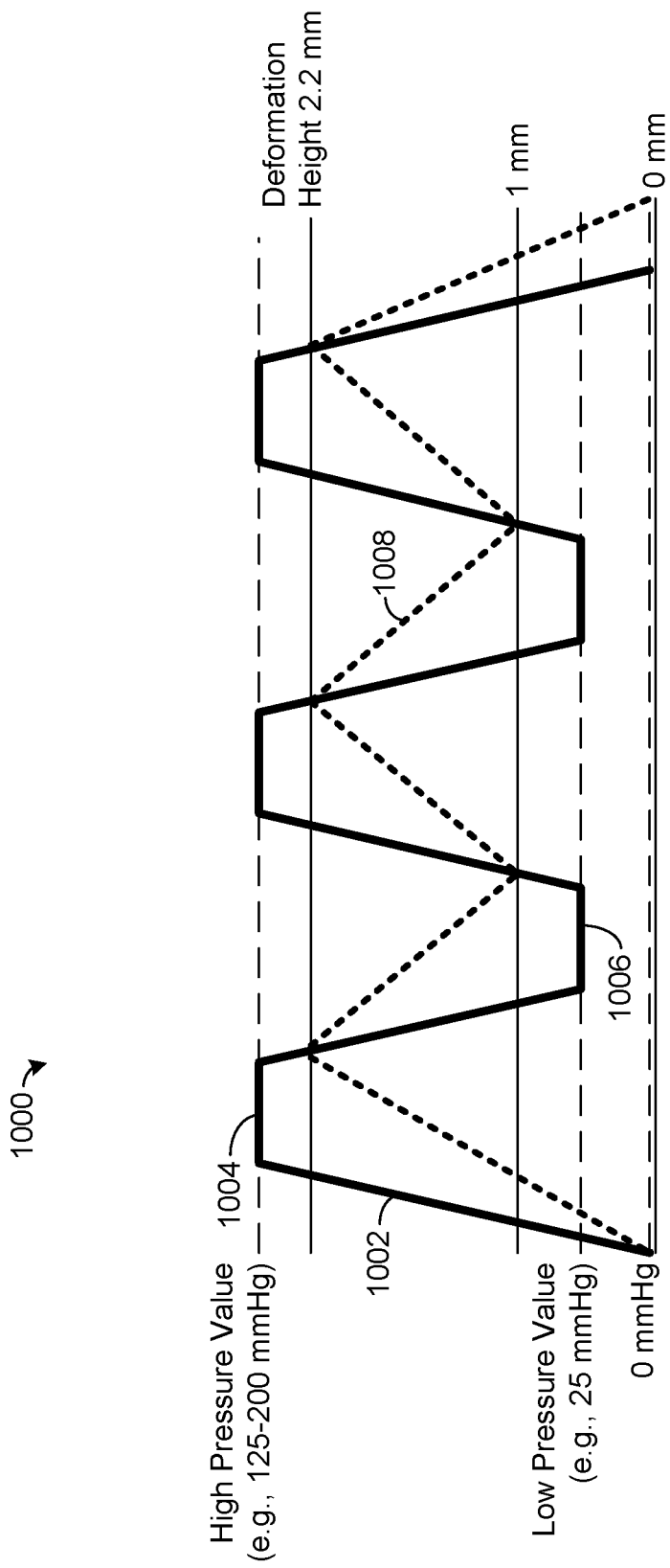
FIG. 10 is a graphical representation of a negative pressure waveform with hold periods, according to an exemplary embodiment.
Figure 11:
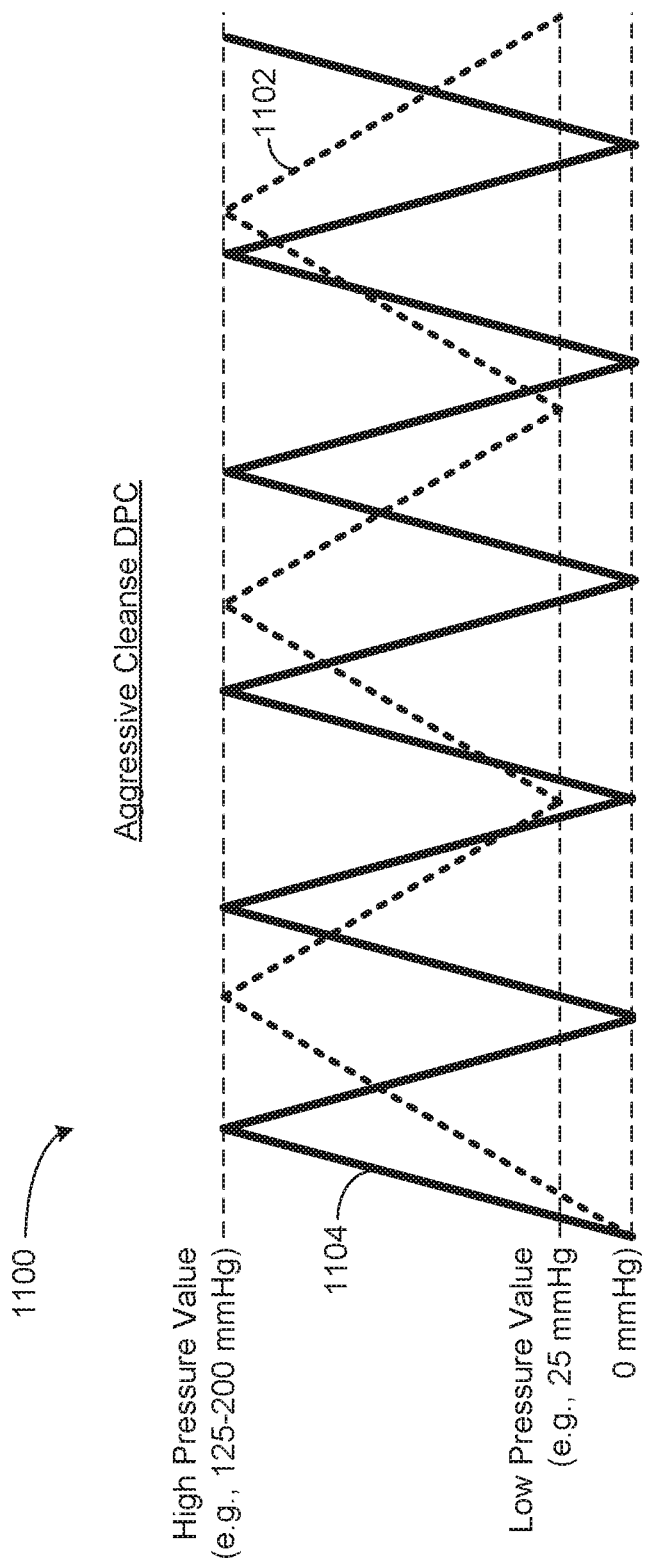
FIG. 11 is a graphical representation of an aggressive cleanse negative pressure waveform, according to an exemplary embodiment.
Figure 12:
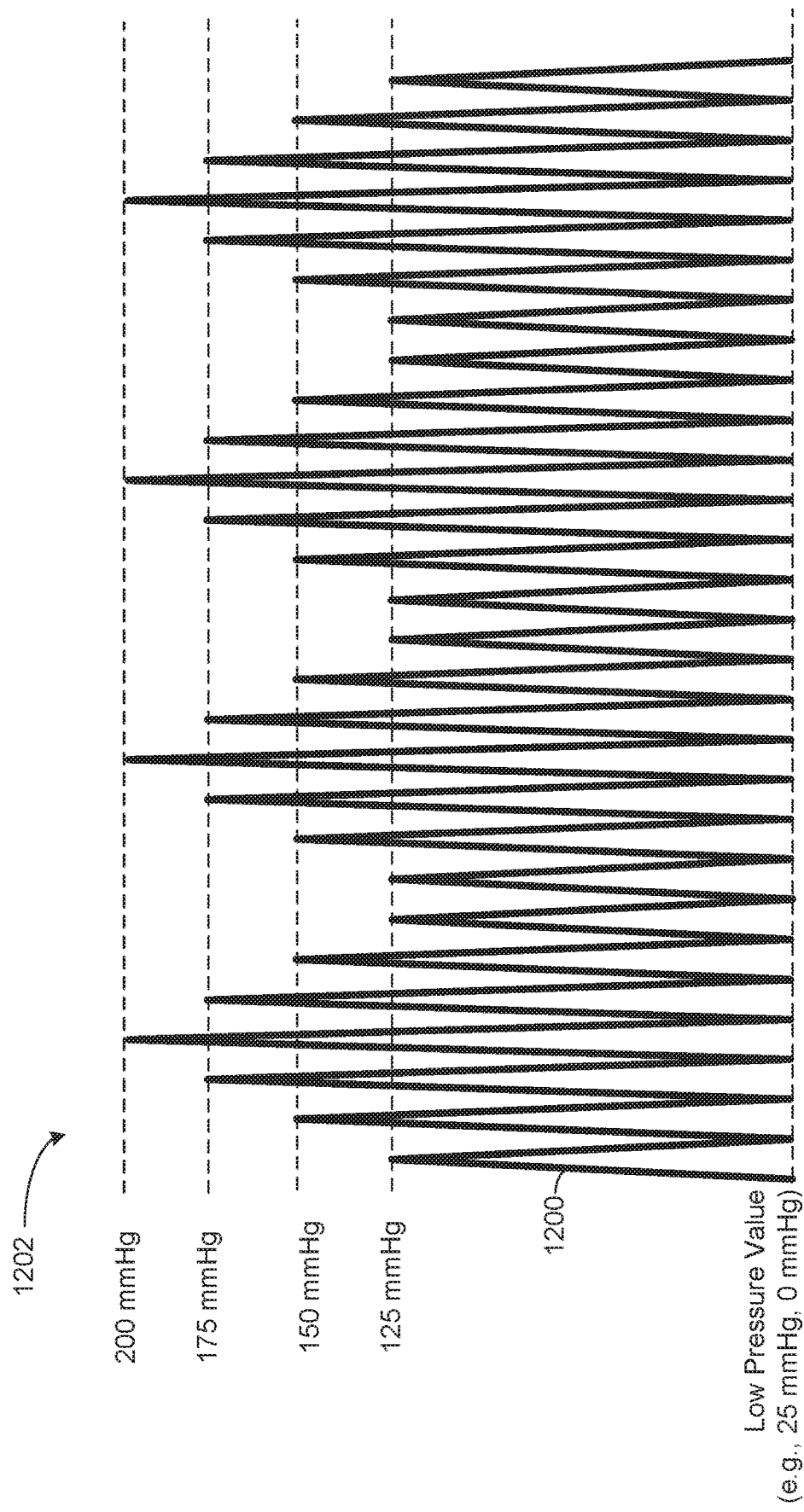
FIG. 12 is a graphical representation of a negative pressure waveform with an oscillating high pressure value, according to an exemplary embodiment.

Although graphs 300 and 302 show linear transitions (i.e., constant slopes) between pressure values, it should be understood that various other pressure trajectories (represented by pressure line 304) may be provided by various embodiments. For example, the pressure line 304 may take a sinusoidal form in alternative embodiments of graph 302. Furthermore, while the example of graph 302 shows substantially equivalent rise times (i.e., the time for pressure to change from the low pressure value to the high pressure value) and fall times (i.e., the time for pressure to change from the high pressure value to the low pressure value), it should be understood that various relative rise times and fall times may be used. For example, a rise time and/or fall time may be selected by a user via the input/output device 118. The control circuit 202 may control the negative pressure pump 112 to achieve the user-selected rise time and/or fall time. Various additional embodiments of dynamic pressure control are illustrated at FIGS. 10-12 and described in detail with reference thereto.

Installation, Soak, and Dynamic Pressure Control Cycle

Figure 4:
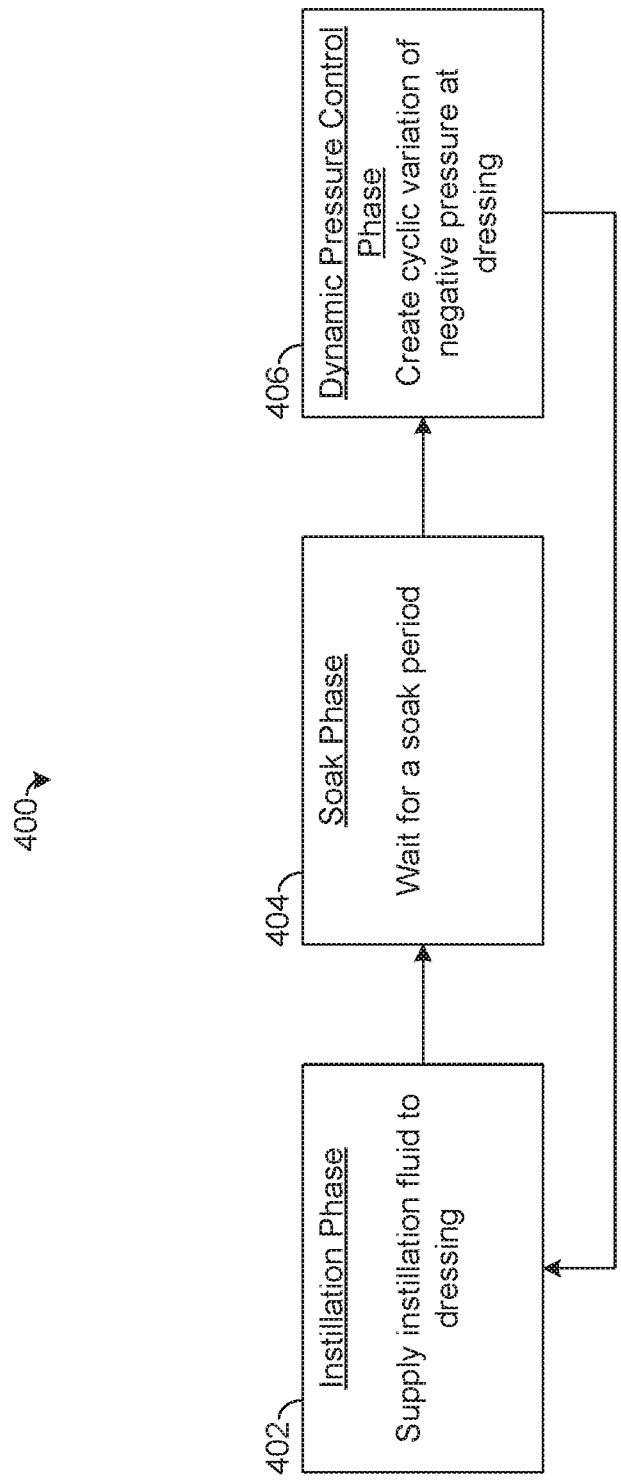
FIG. 4 is a flowchart of a process for negative pressure and instillation wound therapy, according to an exemplary embodiment.

Referring now to FIG. 4, a flowchart depicting a process 400 for treating a wound using the NPIWT system 100 of FIGS. 1-2 is shown, according to an exemplary embodiment. Process 400 is shown as a cycle through three phases, namely an instillation phase 402, a soak phase 404, and a dynamic pressure control phase 406. The control circuit 202 may be configured to control the instillation pump 116 and the negative pressure pump 112 to execute process 400. Advantageously, the process 400 may provide improved wound healing as indicated by experimental results shown in FIG. 5 and described with reference thereto below.

At the instillation phase 402, the control circuit 202 controls the instillation pump 116 to provide instillation fluid from the instillation fluid source 110 to the dressing 104 via the instillation tube 108. At the instillation phase 402, the control circuit 202 may control the instillation pump 116 to provide a particular amount (e.g., volume) of instillation fluid and/or to provide instillation fluid for a particular duration of time. Installation fluid may thereby be placed in contact with the wound bed. The amount of instillation fluid provided at the instillation phase 402 and/or the duration of time of the instillation phase 402 may be user-selectable (e.g., by a doctor, nurse, caregiver, patient) via the input/output device 118 and/or otherwise customizable (e.g., for various wound types, for various types of instillation fluid).

At the soak phase 404, the control circuit 202 provides a soak period between the instillation phase 402 and the dynamic pressure control phase 406. During the soak phase 404, the control circuit 202 controls the instillation pump 116 to prevent additional fluid from being added to the dressing 104 and prevents the negative pressure pump 112 from operating. The soak phase 404 thereby provides a soak period during which the instillation fluid added at the instillation phase 402 can soak into the wound bed, for example to soften, loosen, dissolve, etc. unwanted scar tissue or wound exudate. The duration of the soak period may be user-selectable via the input/output device 118 and/or otherwise customizable (e.g., for various wound types, for various types of instillation fluid). For example, the soak period may have a duration of between thirty seconds and ten minutes.

At the dynamic pressure control phase 406, the control circuit 202 controls the negative pressure pump 112 to create a cyclic variation of negative pressure at the dressing 104. The negative pressure pump 112 may operate to cause the pressure at the dressing 104 to oscillate between a low pressure value and a high pressure value, for example as illustrated by pressure line 304 on graph 302 of FIG. 3. The frequency of such oscillations may vary in various embodiments and/or may be user-selectable via the input/output device 118. The low pressure value, high pressure value, and/or pressure differential may also be customizable (e.g., user-selectable via the input/output device 118). In some embodiments, the instillation pump 116 is controlled to provide instillation fluid to the dressing 104 during the dynamic pressure control phase 406.

During the dynamic pressure control phase 406, the negative pressure pump 112 is controlled to remove air, fluid, and/or debris from the wound bed and the dressing 104. In some cases, the negative pressure pump 112 may remove the instillation fluid added at the instillation phase 402. The negative pressure pump 112 may also remove tissue softened, dissolved, etc. by the instillation fluid during the soak phase 404. Under dynamic pressure control (e.g., as shown on graph 302 of FIG. 3), the cyclic variation of negative pressure may provide additional energy to the wound bed to facilitate debridement and encourage wound healing. The instillation phase 402, the soak phase 404, and the dynamic pressure control phase 406 thereby work together to provide improved wound therapy.

As illustrated by FIG. 4, the control circuit 202 may control the NPIWT system 100 to repeatedly cycle through the sequence of the instillation phase 402, the soak phase 404, and the dynamic pressure control phase 406. Various parameters (e.g., amount of instillation fluid provide, the length of the soak phase, the low pressure value, the high pressure value, the oscillation frequency) of the phases 402 may remain constant between cycles, may vary between cycles, or some combination thereof. Accordingly, the process 400 is highly configurable for various wound types, wound sizes, patients, instillation fluids, dressings 104, etc.

Experimental Results

Figure 5:
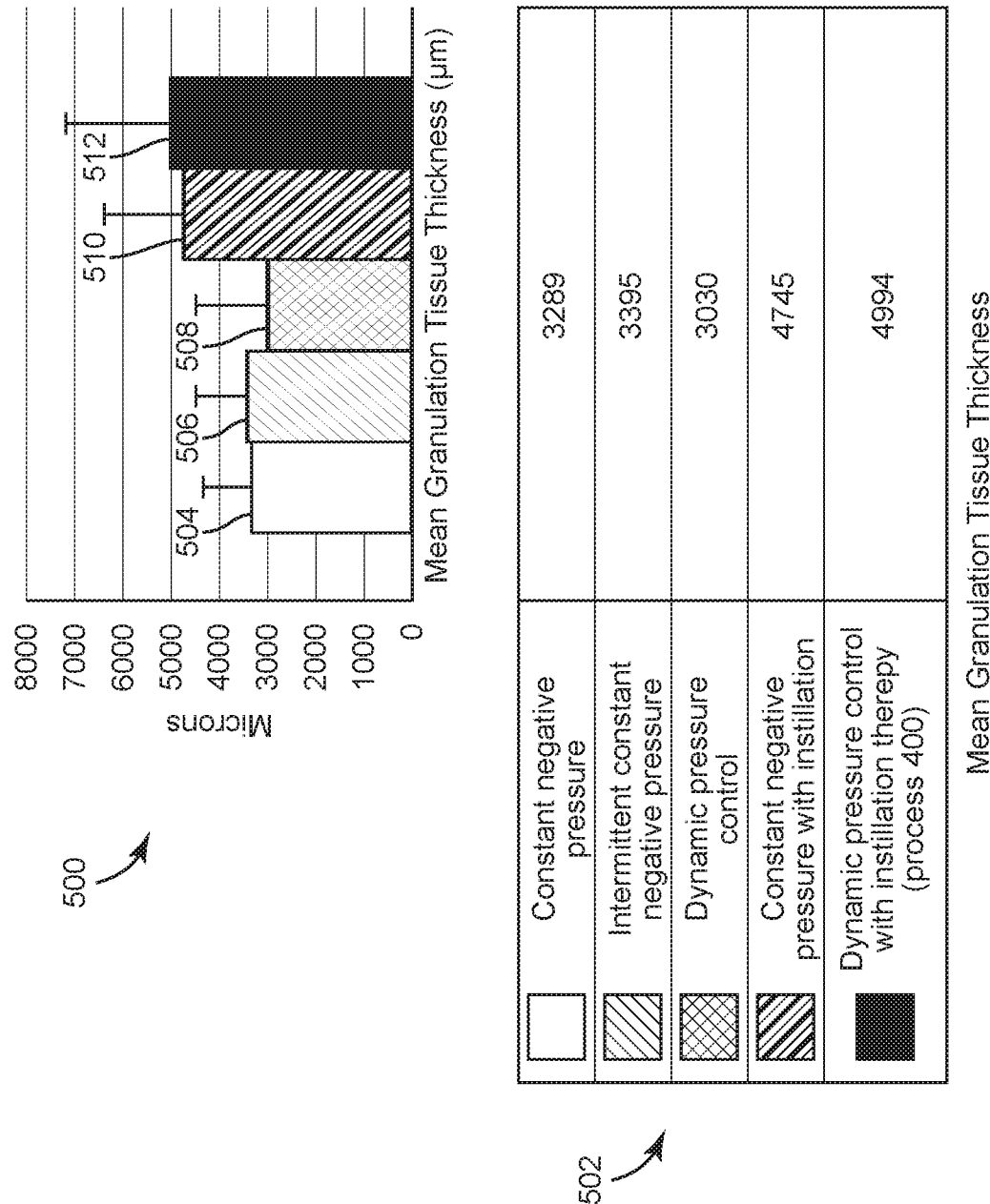
FIG. 5 is an illustration of experimental results using the process of FIG. 4 with the negative pressure and instillation wound therapy system of FIG. 1, according to an exemplary embodiment.

Referring now to FIG. 5, experimental results showing improved wound healing using process 400 and the NPIWT system 100 are shown, according to an exemplary embodiment. An animal study was conducted in which the NPIWT system 100 was used to treat wounds under various control approaches, described below. After a period of time, the thickness of granulation tissue on the wound was then measured, which indicates an amount of wound healing (i.e., thicker granulation tissue corresponds to more healing).

FIG. 5 shows a graph 500 and table 502 that indicate that process 400 may provide higher rates of wound healing than alternative wound therapy approaches. The table 502 displays the data represented in the graph 500. The graph 500 includes a first bar 504 that shows the mean granulation tissue thickness in the experiment for a wound treated by the NPIWT system 100 using constant negative pressure (e.g., 125 mmHg), for example as illustrated by graph 302 of FIG. 3. The graph 500 also includes a second bar 506 that shows the mean granulation tissue thickness in the experiment for a wound treated by the NPIWT system 100 using intermittent constant negative pressure, in which constant negative pressure (e.g., 125 mmHg) is applied for intermittent time periods separated by periods where the negative pressure pump 112 is turned off. The graph 500 includes a third bar 508 that shows the mean granulation tissue thickness in the experiment for a wound treated by the NPIWT system 100 using dynamic pressure control, for example as illustrated by graph 304 of FIG. 3 (e.g., with a low pressure value of 25 mmHg and a high pressure value of 125 mmHg). Bars 504-508 correspond to negative pressure wound therapy without instillation therapy.

The graph 500 also includes a fourth bar 510 that shows the mean granulation tissue thickness in the experiment for a wound treated by the NPIWT system 100 using a combination of instillation therapy and constant negative pressure. The graph 500 also includes a fifth bar 512 that shows the mean granulation tissue thickness for a wound treated by the NPIWT system 100 executing process 400. Accordingly, the fourth bar 510 and the fifth bar 512 correspond to negative pressure wound therapy with instillation therapy.

As shown in the graph 500 of FIG. 5, the fifth bar 512 is the largest, indicating that process 400 facilitates greater wound healing relative to the wound therapy approaches corresponding to the first bar 504, second bar 506, third bar 508, and fourth bar 510.

Dressing with Perforated Layer

Referring now to FIGS. 6-7, detailed views of an embodiment of the dressing 104 are shown, according to an exemplary embodiment. FIG. 6 shows a cross-sectional side view of the dressing 104 while FIG. 7 shows a bottom view of the dressing 104 (i.e., a view of the wound-facing surface of the dressing 104 when applied to a patient). The dressing 104 of FIGS. 6-7 may facilitate debridement and cleansing of a wound bed when used in conjunction with process 400 and/or various other wound therapy approaches described herein. The dressing 104 of FIGS. 6-7 may substantially similar to the dressing(s) shown and described in detail in "WOUND DRESSING WITH SEMI-RIGID SUPPORT TO INCREASE DISRUPTION USING PERFORATED DRESSING AND NEGATIVE PRESSURE WOUND THERAPY, U.S. Provisional Patent Application No. 62/757,365, filed Nov. 8, 2018, incorporated by reference herein in its entirety.

As shown in FIGS. 6-7, the dressing 104 includes a drape 600 coupled to a connection pad 602, an intermediate layer 604 coupled to the drape 600, a perforated layer 606 coupled to the intermediate layer 604, and a wound contact layer 608 coupled to the perforated layer 606. The drape 600 is sealable over a wound bed to couple the dressing 104 to the wound bed in a substantially airtight manner to allow a pressure differential to be maintained across the drape 600. The connection pad 602 is coupled to the drape 600, the vacuum tube 106 and the instillation tube 108. The connection pad 602 is positioned at a passage 610 through the drape 600. The connection pad 602 allows for removal of air, fluid, wound exudate, etc. from the dressing 104 via the vacuum tube 106 and allows for addition of instillation fluid to the dressing 104 via the instillation tube 108.

The drape 600 is positioned along the intermediate layer 604. The intermediate layer 604 may be a support layer and/or a manifolding layer. The intermediate layer 604 allows air, fluid, debris, etc. to flow therethrough, i.e., to flow between the connection pad 602 and the perforated layer 606. The perforated layer 606 is positioned along the intermediate layer 604 and configured to allow a negative pressure to be distributed across the wound bed and to allow fluid, debris, etc. to be pass therethrough. A wound contact layer 608 may be coupled to the perforated layer 606 and may be configured to minimize adherence of the dressing 104 to the wound bed.

The perforated layer 606 includes multiple holes 612 extending therethrough. In various embodiments, various numbers of the holes 612 are arranged in various positions on the perforated layer 606. As described in detail below, when negative pressure is established at the dressing 104, the wound bed may be caused to deform into the holes 612 by the negative pressure. Deformation of the wound bed into the multiple holes 612 may contribute to the breakdown of scar tissue or other unwanted tissue or debris at the wound bed. The perforated layer 606 may thereby facilitate debridement and/or cleansing of the wound bed to promote wound healing.

Wound Bed Deformation

Figure 8:
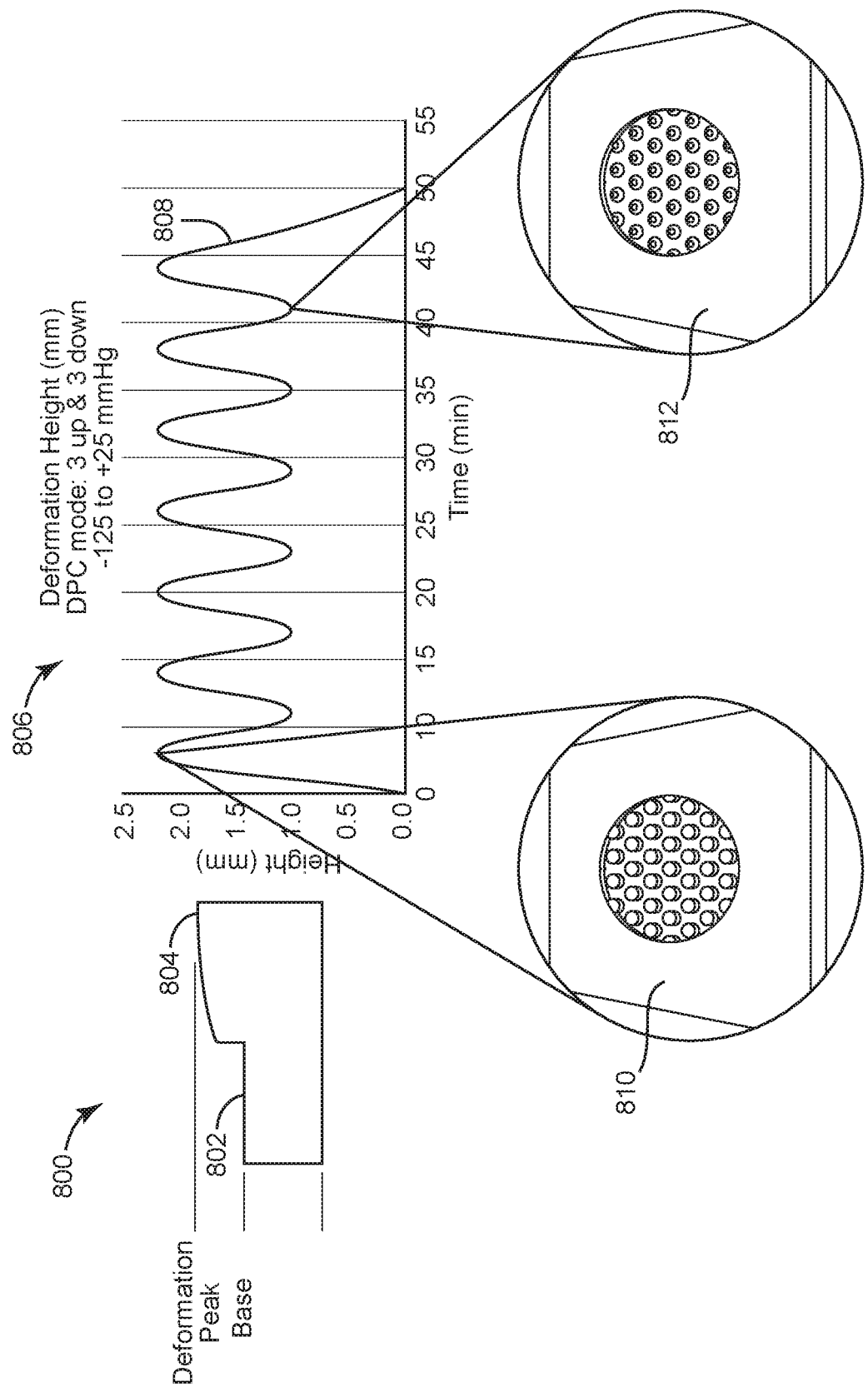
FIG. 8 is a depiction of wound deformation under negative pressure using the dressing of FIGS. 6-7, according to an exemplary embodiment.

Referring now to FIG. 8, a visualization of wound bed deformation into the multiple holes 612 of the perforated layer 606 of the dressing 104 of FIGS. 6-7 under dynamic pressure control is shown, according to an exemplary embodiment. FIG. 8 shows a schematic diagram 800 illustrating that wound bed deformation may be quantified by a measurement of a deformation height from a base 802 of the wound bed to a deformation peak 804 of the wound bed. The deformation height may correspond to a vertical displacement between a point on the wound bed aligned with one of the multiple holes 612 and a point on the wound bed not aligned with one of the multiple holes 612, such that the deformation height measures how far the wound bed extends into the hole 612.

FIG. 8 also includes a graph 806 that illustrates deformation height over time under dynamic pressure control. In the example shown, the control circuit 202 controls the negative pressure pump 112 to provide a cyclic variation of negative pressure at the dressing 104 that acts on the wound bed. In this example, the cyclic variation of negative pressure follows the waveform shown in graph 302 of FIG. 3 and oscillates between a low pressure value of 25 mmHg and a high pressure value of 125 mmHg. Furthermore, in the example shown, the graph 806 is based upon experimental results using a simulated wound material known as Dermasol.

The graph 806 includes a deformation height line 808 that shows that the deformation height approximately tracks the waveform of graph 302. The deformation height increases as negative pressure increases and decreases as negative pressure decrease. In the example shown by the graph 806, the deformation height line 808 reaches maximums at approximately 2.2 millimeters and minimums at approximately 1.0 millimeters. In other words, in the example shown, the wound bed deforms by approximately 2.2 millimeters into the holes 612 under high negative pressure and by approximately 1 millimeter under low negative pressure. FIG. 8 also includes a first depiction 810 of the wound bed while at a maximum deformation and a second depiction 812 of the wound bed while at a minimum deformation.

The deformation of the wound bed may be characterized in terms of the work provided to the wound bed and the elastic energy stored in the deformed tissue. The following paragraphs describe the Applicant's present understanding of the relationship between applied negative pressure, wound bed deformation, work, and elastic energy.

During negative pressure wound therapy, the tissue in the wound bed is displaced by applied pressure. The work W performed by the applied pressure is related to a change in the elastic energy $\Delta U$ stored in the deformation tissue as:

$$W = \Delta U. \tag{1}$$

This relationship can be employed to predict tissue deformations from a given applied pressure. To illustrate this, a simple calculation may be performed using experimentally determined values for a model wound material Dermasol. Given a constant value of the applied pressure P, a model wound bed of initial height L and made of Dermasol with Young's modulus E, a fractional change of length $\Delta L/L$ of a region with cross-sectional area A will occur. The Applicant believes that the work performed by the applied pressure and associated change in tissue elastic energy is given by:

$$W = \int_0^{\Delta V} P dV = PA \int_0^{\Delta L} dy = A(P)\Delta L; \tag{2}$$

$$\Delta U = \int_0^{\Delta L} \left(\frac{A}{L}\right) Ey dy = A\left(\frac{E}{2}\frac{\Delta L}{L}\right)\Delta L.$$

This relationship is validated with the experimentally determined values reported in the following table:

| Measurement | Variable | Value |
|---|---|---|
| Pressure | P | 16665 Pa |
| Young's Modulus | E | 119110 Pa |
| Undeformed Height | L | 14 mm |
| Height Deformation | ΔL | 5 mm |
| Cross-Sectional Area | A | 80 mm² |

These values give:

$$W = (80*10^{-6})(1665)(5*10^{-3}) \approx 7 \; mj; \quad (3)$$

$$\Delta U = (80*10^{-6})\left(\frac{119110}{2}\frac{5}{14}\right)(5*10^{-3}) \approx 9 \; mj.$$

While the work performed by the applied pressure and the elastic energy in the deformed tissue are of the same magnitude, there is an approximately 20% discrepancy. The resolution of this discrepancy will require the following improvements: First, more accurate measurement of the elastic properties of the Dermosol may be required. The Young's modulus and Poisson's ration, the latter having been neglected above in the analysis above for the sake of simplicity, can be accurately determined using an oscillatory rheometer. Second, inclusion of the deformation of the dressing may also be required.

Knowing the elastic properties of Dermosol, the geometry of the wound model, and the applied pressure, the displacement of the wound is calculable. This face is reflected in the relationships by Equations (2), i.e., $$P = \frac{E}{2}\frac{\Delta L}{L} \Rightarrow \Delta L = \frac{2LP}{E}.$$

Here the displacement ΔL is a function of the initial geometry L, the applied pressure P, and the elastic property E. Using more detailed information from the rheometry measurements suggested above and the computational method Finite Element Analysis, the deformation field of the wound model may be calculated. This technique may be a useful tool for optimizing negative pressure wound therapy products, for example the NPIWT system 100 and components thereof.

The total amount of work done on a wound bed may also be calculated using this approach. For example, at 9 mJ per perforation (i.e., as calculated at Equations (3)) and a dressing 104 with twenty-three holes 612, the negative pressure pump 112 does approximately 207 mJ of work on the wound bed per cycle of the cyclic variation of negative pressure (i.e., for each period of the waveform shown on graph 302). If five cycles are provided in a phase (e.g., during the dynamic pressure control phase 406) the work increases to approximately 5*207 mJ=1035 mJ for the phase. The negative pressure pump 112 may therefore do substantially more work on the wound bed under dynamic pressure control than under a constant negative pressure approach.

NPIWT System with Scrub Cycle and Instillation Cycle

Figure 9:
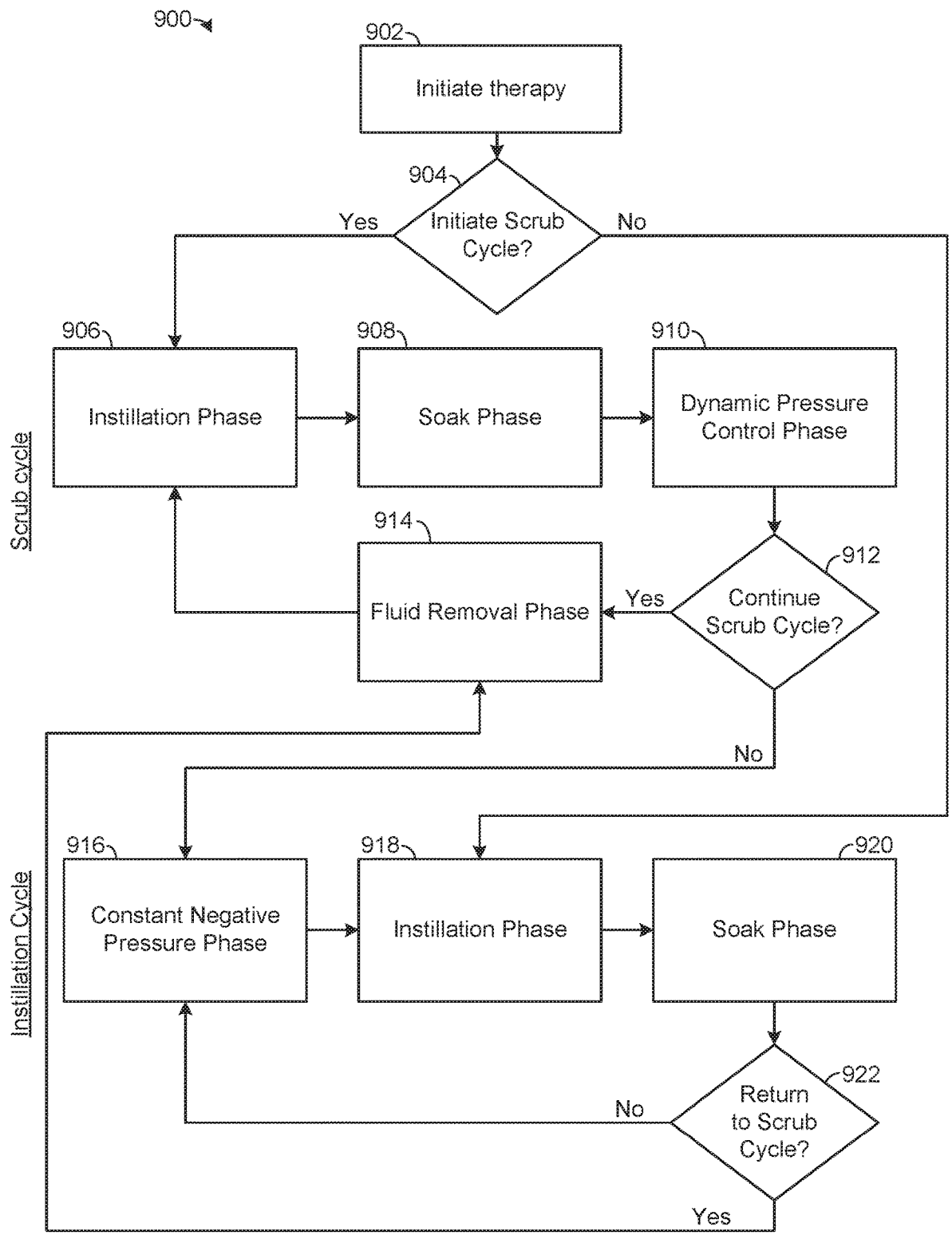
FIG. 9 is a flowchart of a process for negative pressure and instillation wound therapy, according to an exemplary embodiment.

Referring now to FIG. 9, a process 900 for providing wound therapy with the NPIWT system 100 is shown, according to an exemplary embodiment. The control circuit 202 may be configured to control the instillation pump 116 and the negative pressure pump 112 to execute process 900. In some embodiments, the process 900 is carried out with a dressing 104 that includes the perforated layer 606 with holes 612 as in FIGS. 6-7. As described in detail below, provides 900 provides wound therapy having a scrub cycle and an instillation cycle.

At step 902, wound therapy is initiated. The dressing 104 is sealed over a wound bed and coupled to the therapy unit 102 by the vacuum tube 106 and the instillation tube 108. To cause wound therapy to be initiated, a user may input a command via the input/output device 118 to initiate therapy (e.g., to turn on). In response, the control circuit 202 may be activated and may proceed to control the instillation pump 116 and the negative pressure pump 112 as described in the following paragraphs.

At step 904, the control circuit 202 determines whether to initiate a scrub cycle. The scrub cycle includes steps 906-914 of process 900, described in detail below. The scrub cycle provides enhanced scrubbing, debridement, cleansing, etc. of the wound bed. Accordingly, the control circuit 202 may determine to initiate the scrub cycle based on an indication that the wound bed requires scrubbing, debridement, cleansing, etc., for example based on information about the type of wound being treated. In some embodiments, the control circuit 202 causes the input/output device 118 to prompt a user to select whether to initiate the scrub cycle If the control circuit 202 determines that the scrub cycle will be initiated, at step 906 the control circuit 202 controls the instillation pump 116 to provide an instillation phase. During step 906 (i.e., during the instillation phase), instillation fluid is added to the dressing 104. The control circuit 202 may control the instillation pump 116 to provide a particular amount of the instillation fluid to the dressing 104 and/or provide instillation fluid to the dressing 104 for a particular amount of time. The amount of fluid added and/or the duration of the instillation phase may be user-selectable via the input/output device 118 and/or otherwise customizable (e.g., for various wound types, for various types of instillation fluid).

At step 908, the instillation fluid added at step 906 is allowed to soak into the wound bed in a soak phase. During the soak phase (i.e., at step 908), the control circuit 202 may control the instillation pump 116 to prevent instillation fluid from being added to the dressing 104 and may prevent operation of the negative pressure pump 112. The control circuit 202 thereby provides a soak period during which the instillation fluid added at step 906 can soak into the wound bed, for example to soften, loosen, dissolve, etc. unwanted scar tissue or wound exudate. The duration of the soak period may be user-selectable via the input/output device 118 and/or otherwise customizable (e.g., for various wound types, for various types of instillation fluid). For example, the soak period may have a duration of between thirty seconds and ten minutes.

At step 910, the control circuit 202 controls the negative pressure pump 112 to provide a cyclic variation of negative pressure at the dressing 104 and the wound bed in a dynamic pressure control phase. In embodiments where the dressing 104 includes holes 612 as in FIG. 6, the wound bed may be deformed into the holes 612 during step 910. For example, the wound deformation height may increase as the negative pressure at the dressing 104 increases and may decrease as the negative pressure at the dressing 104 decreases. In some embodiments, as described above with reference to FIG. 8, the negative pressure may do work on the wound bed in a range of approximately 7 mJ to 9 mJ per hole 612 for each cycle of the cyclic variation of negative pressure (e.g., for each period of the waveform shown on graph 302 of FIG. 3).

In various embodiments, the negative pressure may do work on the wound bed in a range of approximately 2 mJ and 30 mJ per hole 612 for each cycle. As another example, with a diameter of the holes 612 of approximately 10 mm and a negative pressure of 125 mmHg, work in a range of approximately 2 mJ to 3 mJ can be achieved. Higher amounts of work may be provided by increasing the size of the holes 612 and by increasing the pressure (in absolute value). The combination of dynamic pressure control and the perforated layer 606 of the dressing 104 provides increased scrubbing and debridement of the wound bed at step 910. Accordingly, step 910 may cause the separation of a substantial amount of debris, scar tissue, etc. from the wound bed.

In some embodiments, the dynamic pressure control phase of step 910 includes controlling the negative pressure pump 112 to provide a waveform having hold periods at high pressure values and/or low pressure values, for example as shown in FIG. 10 and described with reference thereto. In some embodiments, the dynamic pressure control phase of step 910 includes controlling the negative pressure pump 112 to provide an aggressive cleanse waveform, for example as shown in FIG. 11 and described with reference thereto. In some embodiments, the dynamic pressure control phase of step 910 includes varying a high pressure value and/or pressure differential of the cyclic variation of negative pressure over time, for example as shown in FIG. 12 and described in detail with reference thereto. The duration of step 910 may be user-selectable and/or otherwise customizable. In various embodiments, the dynamic pressure control phase may have a duration between one minute and three hours, for example three minutes. In some embodiments, the dynamic pressure control phase of step 910 includes controlling the instillation pump 116 to provide instillation fluid to the dressing 104 during step 910.

At step 912, the control circuit 202 determines whether to continue the scrub cycle. In some embodiments, the control circuit 202 may determine whether to continue the scrub cycle based on a preset number of desired scrub cycles. For example, the control circuit 202 may count the number of times that steps 906-910 are completed and continue the scrub cycle until that number reaches a preset threshold (e.g., a threshold number input by a user). In other embodiments, at step 912 the control circuit 202 may cause the input/output device 118 to prompt a user for input indicating whether to continue the scrub cycle and determine whether to content the scrub cycle based on the user input.

If the control circuit 202 makes a determine a determination to continue the scrub cycle, at step 914 the control circuit 202 controls the negative pressure pump 112 to provide a fluid removal phase. During the fluid removal phase, the negative pressure pump 112 is controlled to remove fluid, debris, etc. from the dressing 104. The fluid, debris, etc. removed from the dressing 104 by the negative pressure pump 112 at step 914 may include the instillation fluid added at step 906 and debris, scar tissue, etc. separated from the wound bed at step 910. Step 914 thereby provides a fluid removal phase in which undesirable fluid and debris is removed from the dressing 104 and prepares NPIWT system 100 to repeat the scrub cycle.

Following the fluid removal phase of step 914, the process 900 returns to cycle through step 906, step 908, and step 910. The scrub cycle (i.e., steps 906-914) may be repeated any number of times until, at an instance of step 912, the control circuit 202 determines that the scrub cycle will no longer be continued.

If the control circuit 202 determines that the scrub cycle will not be continued at step 912, process 900 proceeds to step 916 where a constant negative pressure phase is provided to initiate an instillation cycle (steps 916-920). At step 916, the control circuit 202 controls the negative pressure pump 112 to provide an approximately constant negative pressure (e.g., 125 mmHg, 100 mmHg, etc.), for example as shown in graph 300 of FIG. 3. The control circuit 202 may receive pressure measurements from the sensor(s) 200 for use as feedback in a control loop for the negative pressure pump 112. The negative pressure pump 112 may remove fluid, debris, etc. provided to the dressing 104 and/or separated or exuded from the wound bed. The duration of the constant negative pressure phase may be user-selectable via input/output device 118 and/or otherwise customizable.

At step 918, the control circuit 202 provides an instillation phase by controlling the instillation pump 116 to provide instillation fluid to the dressing 104. In some embodiments, the control circuit 202 behaves substantially the same at step 918 is as at step 906. The instillation pump 116 may be controlled to provide a particular amount of the instillation fluid to the dressing 104 and/or provide instillation fluid to the dressing 104 for a particular amount of time. The amount of fluid added and/or the duration of the instillation phase may be user-selectable via the input/output device 118 and/or otherwise customizable (e.g., for various wound types, for various types of instillation fluid).

At step 920, the control circuit 202 provides a soak phase by controlling the instillation pump 116 to prevent the addition of instillation fluid to the dressing 104 for a soak period and to prevent operation of the negative pressure pump 112 for the soak period. In some embodiments, the control circuit 202 behaves substantially the same at step 920 as at step 908. The control circuit 202 provides a soak period during which the instillation fluid added at step 918 can soak into the wound bed, for example to soften, loosen, dissolve, etc. unwanted scar tissue or wound exudate or to provide other therapy to the wound bed. The duration of the soak period may be user-selectable via the input/output device 118 and/or otherwise customizable (e.g., for various wound types, for various types of instillation fluid). For example, the soak period may have a duration of between thirty seconds and ten minutes.

At step 922, the control circuit 202 determines whether to return to the scrub cycle or to repeat the instillation cycle (i.e., steps 916-920). For example, the control circuit 202 may repeat the instillation cycle for a preset or user-selected number of times before repeating the instillation cycle. In some embodiments, at step 922 the control circuit 202 causes the input/output device 118 to prompt a user to input an indication of whether to return to the scrub cycle or to repeat the instillation cycle. If the control circuit 202 makes a determination to not return to the scrub cycle, process 900 returns to step 916 to restart the instillation cycle. If the control circuit 202 makes a determination to return to the scrub cycle, the process 900 returns to step 914 to reenter the scrub cycle.

The control circuit 202 may thereby control the instillation pump 116 and the negative pressure pump 112 to provide various numbers of scrub cycles and instillation cycles in various orders. Furthermore, it should be understood that the duration of each phase (i.e., steps 906, 908, 910, 914, 916, 918, and 920) is highly variable. For example, the duration of one or more phases may change between sequential cycles. Various other parameters (e.g., low pressure values, high pressure values, frequency, waveform, amount of instillation fluid, etc.) may also vary between cycles. Accordingly, process 900 is highly configurable and customizable to provide negative pressure and instillation wound therapy well suited to a variety of wound types, patients, stages of healing, etc.

Pressure Control Waveforms

Referring now to FIG. 10 an alternative embodiment of a dynamic pressure control waveform is shown, according to an exemplary embodiment. FIG. 10 shows a graph 1000 that includes a pressure line 1002 that charts negative pressure over time. In the embodiment of FIG. 10, the pressure line 1002 increases from atmospheric pressure to a high pressure value (e.g., 125 mmHg of negative pressure) and remains at the high pressure value for a first hold period 1004 before decreasing to a low pressure value (e.g., 25 mmHg). The pressure line 1002 then remains at the low pressure value for a second hold period 1006 before returning to the high pressure value. This cycle may be repeated any number of times. The graph 1000 also includes a deformation height line 1008 that charts the deformation height of the wound bed over time in response to the changes in negative pressure.

The control circuit 202 may control the negative pressure pump 112 to provide negative pressure that substantially tracks the pressure line 1002 of FIG. 10. In such a case, the first hold period 1004 may allow time for the wound bed to reach a maximum deformation height (e.g., shown as 2.2 mm) before the negative pressure is reduced. The second hold period 1006 may allow the wound bed to reach a minimum deformation height (e.g., shown as 1 mm) before the negative pressure is increased. The dynamic pressure control waveform of FIG. 10 thereby accounts for a lag time between a change in pressure and a change in tissue deformation, which may help to maximize the amount of work done on the wound bed. In various embodiments, the first hold period 1004 and the second hold period 1006 may have the same duration or different durations. In various embodiments, the maximum deformation height and the minimum deformation height have various values. A dynamic pressure control approach having hold periods 1004, 1006 may be applied in process 400 (at dynamic pressure control phase 406) and/or process 900 (at dynamic pressure control phase 910), and may be used with the perforated layer 606 of the dressing 104.

Referring now to FIG. 11, a graphical representation of aggressive cleanse pressure control is shown, according to an exemplary embodiment. FIG. 11 includes a graph 1100 that charts negative pressure over time. Graph 1100 includes a dynamic pressure control line 1102 and an aggressive cleanse pressure control line 1104. The dynamic pressure control line 1102 corresponds to the pressure line 304 on graph 302 of FIG. 3 and is included in graph 1100 for the sake of comparison to the aggressive cleanse pressure control line 1104. The dynamic pressure control line 1102 shows that, under dynamic pressure control, the control circuit 202 may control the negative pressure pump 112 to draw a negative pressure at the dressing 104 from atmospheric pressure to a high pressure value, allow the negative pressure to return to a low pressure value, draw the negative pressure back to the high pressure value, and so on. In other words, the dynamic pressure control line 1102 illustrates a waveform having a frequency and an amplitude (i.e., a pressure differential). The amplitude of the dynamic pressure control line 1102 ranges from a minimum at the low pressure value to a maximum at the high pressure value.

The aggressive cleanse pressure control line 1104 illustrates an alternative pressure control approach which may do an increased amount of work on the wound bed and provide for increased debridement of the wound bed. The aggressive cleanse pressure control line 1104 illustrates that the control circuit 202 may control the negative pressure pump 112 to draw a negative pressure at the dressing 104 from atmospheric pressure to a high pressure value, allow the dressing 104 to return to atmospheric pressure, draw negative pressure at the dressing 104 from atmospheric pressure to a high pressure value, allow the dressing 104 to return to atmospheric pressure, and so on. The control circuit 202 thereby controls the negative pressure pump 112 to provide a cyclic variation of negative pressure that oscillates between a high pressure value and atmospheric pressure.

Accordingly, the aggressive cleanse pressure control line 1104 depicts a waveform with a greater amplitude (i.e., greater pressure differential) as compared to the waveform of the dynamic pressure control line 1102. Furthermore, the aggressive cleanse pressure control line 1104 depicts a waveform with a greater frequency (shorter period) as compared to the waveform of the dynamic pressure control line 1102. Because of the greater amplitude and frequency, aggressive cleanse pressure control may provide more energy to the wound bed and cause increased scrubbing and debridement of the wound bed. In some embodiments, aggressive cleanse pressure control may be used in process 400 (at dynamic pressure control phase 406) and/or process 900 (at dynamic pressure control phase 910). In some embodiments, aggressive cleanse pressure control is used with the perforated layer 606 of the dressing 104.

Referring now to FIG. 12, a graphical representation of dynamic pressure control with a variable high pressure value is shown, according to an exemplary embodiment. As illustrated by pressure line 1200 on graph 1202 of FIG. 12, dynamic pressure control may provide a cyclic variation of negative pressure that includes multiple cycles between a low pressure value and a high pressure value. In the example of FIG. 12, the high pressure value changes between a first cycle and a second cycle of the multiple cycles. In various embodiments, the pressure differential may change between the first and second cycles in a variety of ways. In the example of FIG. 12, the high pressure value oscillates over time between a minimum high pressure value (e.g., 125 mmHg) and a maximum high pressure value (e.g., 200 mmHg). The control circuit 202 may be configured to control the negative pressure pump 112 to provide the negative pressure depicted by the pressure line 1200 of FIG. 12. Changing the high pressure value over time as in FIG. 12 may facilitate wound healing by preventing the wound bed from adapting to a particular high pressure value. Dynamic pressure control with a variable high pressure value as illustrated by pressure line 1200 may be used in process 400 (at dynamic pressure control phase 406) and/or process 900 (at dynamic pressure control phase 910). In some embodiments, dynamic pressure control with a variable high pressure value is used with the perforated layer 606 of the dressing 104.

FIGS. 3 and 10-12 show various dynamic pressure control waveforms according to various embodiments. The control circuit 202 may be configured to control the negative pressure pump 112 to provide negative pressure at the dressing 104 that substantially tracks one or more of these waveforms and/or combinations thereof. For example, the hold periods of the pressure line 1002 FIG. 10 may be combined with the variable high pressure value of the pressure line 1200 of FIG. 12 to provide hold periods at varying high pressure values. Many such combinations and adaptations are possible.

Configuration of Exemplary Embodiments

Although the figures show a specific order of method steps, the order of the steps may differ from what is depicted.

Also two or more steps can be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, calculation steps, processing steps, comparison steps, and decision steps.

The construction and arrangement of the systems and methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements can be reversed or otherwise varied and the nature or number of discrete elements or positions can be altered or varied. Accordingly, all such modifications are intended to be included within the scope of the present disclosure. The order or sequence of any process or method steps can be varied or re-sequenced according to alternative embodiments. Other substitutions, modifications, changes, and omissions can be made in the design, operating conditions and arrangement of the exemplary embodiments without departing from the scope of the present disclosure.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the disclosure as recited in the appended claims.

As used herein, the term "circuit" may include hardware structured to execute the functions described herein. In some embodiments, each respective "circuit" may include machine-readable media for configuring the hardware to execute the functions described herein. The circuit may be embodied as one or more circuitry components including, but not limited to, processing circuitry, network interfaces, peripheral devices, input devices, output devices, sensors, etc. In some embodiments, a circuit may take the form of one or more analog circuits, electronic circuits (e.g., integrated circuits (IC), discrete circuits, system on a chip (SOCs) circuits, etc.), telecommunication circuits, hybrid circuits, and any other type of "circuit." In this regard, the "circuit" may include any type of component for accomplishing or facilitating achievement of the operations described herein. For example, a circuit as described herein may include one or more transistors, logic gates (e.g., NAND, AND, NOR, OR, XOR, NOT, XNOR, etc.), resistors, multiplexers, registers, capacitors, inductors, diodes, wiring, and so on).

The "circuit" may also include one or more processors communicably coupled to one or more memory or memory devices. In this regard, the one or more processors may execute instructions stored in the memory or may execute instructions otherwise accessible to the one or more processors. In some embodiments, the one or more processors may be embodied in various ways. The one or more processors may be constructed in a manner sufficient to perform at least the operations described herein. In some embodiments, the one or more processors may be shared by multiple circuits (e.g., circuit A and circuit B may comprise or otherwise share the same processor which, in some example embodiments, may execute instructions stored, or otherwise accessed, via different areas of memory). Alternatively or additionally, the one or more processors may be structured to perform or otherwise execute certain operations independent of one or more co-processors. In other example embodiments, two or more processors may be coupled via a bus to enable independent, parallel, pipelined, or multi-threaded instruction execution. Each processor may be implemented as one or more general-purpose processors, application specific integrated circuits (ASICs), field programmable gate arrays (FPGAs), digital signal processors (DSPs), or other suitable electronic data processing components structured to execute instructions provided by memory. The one or more processors may take the form of a single core processor, multi-core processor (e.g., a dual core processor, triple core processor, quad core processor, etc.), microprocessor, etc. In some embodiments, the one or more processors may be external to the apparatus, for example the one or more processors may be a remote processor (e.g., a cloud based processor). Alternatively or additionally, the one or more processors may be internal and/or local to the apparatus. In this regard, a given circuit or components thereof may be disposed locally (e.g., as part of a local server, a local computing system, etc.) or remotely (e.g., as part of a remote server such as a cloud based server). To that end, a "circuit" as described herein may include components that are distributed across one or more locations. The present disclosure contemplates methods, systems and program products on any machine-readable media for accomplishing various operations. The embodiments of the present disclosure can be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. Combinations of the above are also included within the scope of machine-readable media. Machine-executable instructions include, for example, instructions and data which cause a general purpose computer, special purpose computer, or special purpose processing machines to perform a certain function or group of functions.

What is claimed is:
1. A wound therapy system, comprising:
a dressing comprising:
a wound contact layer configured to minimize adherence of the dressing to a wound bed;

a perforated layer comprising a plurality of holes extending therethrough, the wound contact layer configured to be coupled to the perforated layer;

an intermediate layer configured to manifold fluid, the perforated layer configured to be coupled to the intermediate layer on a side opposite the wound contact layer; and a drape configured to be disposed over the intermediate layer and seal over the wound bed;

an installation pump fluidly communicable with the dressing and configured to provide instillation fluid to the dressing;

a negative pressure pump fluidly communicable with the dressing and configured to remove air from the dressing; and a control circuit communicably coupled to the instillation pump and the negative pressure pump and configured to:

control the instillation pump and the negative pressure pump to perform at least one scrub cycle, the scrub cycle comprising:

controlling the instillation pump to provide a first amount of the instillation fluid to the dressing;

providing a first soak period; and controlling the negative pressure pump to provide a cyclic variation of negative pressure at the dressing to generate cyclic deformation of the wound bed into the perforated layer at the plurality of holes between a first height relative to surrounding tissue and a second height relative to surrounding tissue; and control the instillation pump and the negative pressure pump to perform at least one instillation cycle, the instillation cycle comprising:

controlling the negative pressure pump to provide a constant negative pressure;

controlling the instillation pump to provide a second amount of the instillation fluid; and providing a second soak period.

2. The wound therapy system of claim 1, wherein the cyclic variation of negative pressure comprises an oscillation of the pressure at the dressing across a pressure differential.

3. The wound therapy system of claim 2, wherein the pressure differential is approximately 100 mmHg.

4. The wound therapy system of claim 2, wherein the pressure differential is within a range between approximately 5 mmHg and 300 mmHg.

5. The wound therapy system of claim 2, wherein the cyclic variation of negative pressure comprises a first cycle and a second cycle; and wherein the pressure differential changes between the first cycle and the second cycle.

6. The wound therapy system of claim 2, wherein the pressure differential oscillates over time.

7. The wound therapy system of claim 2, wherein the pressure differential is user-selectable.

8. The wound therapy system of claim 1, wherein a frequency of the cyclic variation of negative pressure is user-selectable.

9. The wound therapy system of claim 1, wherein the cyclic variation of negative pressure comprises a plurality of cycles; and wherein each cycle does an amount of work within a range between approximately 2 mJ and 30 mJ for each of the plurality of holes.

10. The wound therapy system of claim 1, wherein the control circuit is configured to simultaneously control the negative pressure pump to provide the cyclic variation of negative pressure at the dressing and control the instillation pump to provide the first amount of the instillation fluid to the dressing.

11. The wound therapy system of claim 1, wherein at least one of the first amount of the instillation fluid, the second amount of the instillation fluid, the first soak period, and the second soak period are user-selectable.

12. The wound therapy system of claim 1, wherein the control circuit is further configured to repeatedly cycle through sequentially controlling the instillation pump to provide the first amount of the instillation fluid to the dressing, providing the first soak period, and controlling the negative pressure pump to provide the cyclic variation of negative pressure at the dressing.

13. The wound therapy system of claim 1, wherein the control circuit is further configured to repeatedly cycle through sequentially controlling the instillation pump to provide the, first amount of the instillation fluid to the dressing, providing the first soak period, controlling the negative pressure pump to provide the cyclic variation of negative pressure at the dressing, controlling the negative pressure pump to provide the constant negative pressure to the wound bed; controlling the instillation pump to provide a second amount of the instillation fluid: and providing a second soak period.

14. A method of treating a wound, comprising:
providing an instillation pump in fluid communication with a dressing, the dressing comprising:
a wound contact layer configured to minimize adherence of the dressing to a wound bed;
a perforated layer comprising a plurality of holes extending therethrough, the wound contact layer configured to be coupled to the perforated layer;
an intermediate layer configured to manifold fluid, the perforated layer configured to be coupled to the intermediate layer on a side opposite the wound contact layer; and
a drape configured to be disposed over the intermediate layer and seal over the wound bed;
providing a negative pressure pump in fluid communication with the dressing;
providing at least one scrub cycle, the at least one scrub cycle comprising:
supplying, by the instillation pump, a first amount of the instillation fluid to the dressing;
waiting for a first soak period; and
operating the negative pressure pump to create a cyclic variation of negative pressure at the dressing and generating cyclic deformation of the wound bed into the perforated layer at the plurality of holes between a first height relative to surrounding tissue and a second height relative to surrounding tissue; and
providing at least one instillation cycle, the at least one instillation cycle comprising:
controlling the negative pressure pump to provide a constant negative pressure;
controlling the instillation pump to provide a second amount of the instillation fluid; and
providing a second soak period.

15. The method of claim 14, wherein the cyclic variation of negative pressure comprises an oscillation of the pressure at the dressing across a pressure differential.

16. The method of claim 15, wherein the pressure differential is approximately 100 mmHg.

17. The method of claim 15, wherein the pressure differential is in a range between approximately 5 mmHg and 300 mmHg.

18. The method of claim 15, wherein the cyclic variation of negative pressure comprises a first cycle and a second cycle; and
the method comprises changing the pressure differential between the first cycle and the second cycle.

19. The method of claim 15, comprising oscillating the pressure differential over time.

20. The method of claim of claim 15, comprising receiving a user selection of the pressure differential.

21. The method of claim 14, comprising receiving a user selection of a frequency of the cyclic variation of negative pressure.

22. The method of claim 14, comprising doing an amount of work on the wound bed within a range between approximately 2 mJ and 30 mJ for each of the plurality of holes for each of multiple cycles of the cyclic variation of negative pressure.

23. The method of claim 14, comprising simultaneously operating the negative pressure pump to create the cyclic variation of negative pressure at the dressing and controlling the instillation pump to provide the first amount of the instillation fluid to the dressing.

24. The method of claim 14, comprising receiving a user selection of at least one of the first amount of the instillation fluid, the second amount of the instillation fluid, the first soak period, or the second soak period.

25. The method of claim 16, comprising repeatedly cycling through sequentially supplying, by the instillation pump, the first amount of the instillation fluid to the dressing, waiting for the first soak period, and operating the negative pressure pump to create the cyclic variation of negative pressure at the dressing.

26. The method of claim 14, comprising repeatedly cycling through sequentially supplying, by the instillation pump, the first amount of the instillation fluid to the dressing, waiting for the first soak period, operating the negative pressure pump to create the cyclic variation of negative pressure at the dressing, operating the negative pressure pump to create the constant negative pressure at the dressing; controlling the instillation pump to provide a second amount of the instillation fluid; and providing a second soak period.

27. A wound therapy system, comprising:
a dressing comprising:
a wound contact layer configured to minimize adherence of the dressing to a wound bed;
a perforated layer comprising a plurality of holes extending therethrough, the wound contact layer configured to be coupled to the perforated layer;
an intermediate layer configured to manifold fluid, the perforated layer configured to be coupled to the intermediate layer on a side opposite the wound contact layer; and
a drape configured to be disposed over the intermediate layer and seal over the wound bed;
an instillation pump fluidly communicable with the dressing and configured to provide instillation fluid to the dressing;
a negative pressure pump fluidly communicable with the dressing and configured to remove air from the dressing; and
a control circuit communicably coupled to the instillation pump and the negative pressure pump and configured to:
provide at least one scrub cycle, the at least one scrub cycle comprising:
controlling the instillation pump to provide a first amount of the instillation fluid to the dressing;
providing a first soak period; and
controlling the negative pressure pump to provide a variation of negative pressure at the dressing, the variation characterized by a waveform, the variation of negative pressure generating variation in deformation of the wound bed into the perforated layer at the plurality of holes between a first height relative to surrounding tissue and a second height relative to surrounding tissue; and
provide at least one instillation cycle, the at least one instillation cycle comprising:
controlling the negative pressure pump to provide a constant negative pressure;
controlling the instillation pump to provide a second amount of the instillation fluid; and
providing a second soak period.

28. The wound therapy system of claim 27, wherein the waveform comprises:
an amplitude having a maximum at a high pressure value and a minimum at a low pressure value; and
a frequency.

29. The wound therapy system of claim 28. wherein the amplitude is variable in a repeating pattern.

30. The wound therapy system of claim 28, wherein the frequency is variable in a repeating pattern.

31. The wound therapy system of claim 28, wherein:
the amplitude is variable in a first repeating pattern; and
the frequency is variable in a second repeating pattern.

32. The wound therapy system of claim 27, wherein the waveform is user-selectable.

33. The wound therapy system of claim 27, wherein the control circuit is configured to simultaneously control the negative pressure pump to provide the variation of negative pressure at the dressing and control the instillation pump to provide the first amount of the instillation fluid to the dressing.

* * * * *